United States Patent
Ahmed et al.

(10) Patent No.: US 8,217,167 B2
(45) Date of Patent: Jul. 10, 2012

(54) PHENANTHRYLPHENOL LINKED PYRROLO [2, L-C] [L, 4] BENZODIAZEPINE HYBRIDS AS POTENTIAL ANTITUMOUR AGENTS AND PROCESS FOR THE PREPARATION THEREOF

(75) Inventors: Kamal Ahmed, Hyderabad (IN); Sreekanth Kokkonda, Hyderabad (IN); Praveen Kumar Pogula, Hyderabad (IN); Balakishan Gorre, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 12/922,123

(22) PCT Filed: Mar. 12, 2009

(86) PCT No.: PCT/IN2009/000168
§ 371 (c)(1),
(2), (4) Date: May 12, 2011

(87) PCT Pub. No.: WO2009/113109
PCT Pub. Date: Sep. 17, 2009

(65) Prior Publication Data
US 2011/0207924 A1    Aug. 25, 2011

(30) Foreign Application Priority Data

Mar. 11, 2008  (IN) .............................. 602/DEL/2008

(51) Int. Cl.
*C07D 487/04*  (2006.01)
(52) U.S. Cl. ..................................................... 540/496
(58) Field of Classification Search .................. 540/496
See application file for complete search history.

(56) References Cited

U.S. PATENT DOCUMENTS
2005/0222133 A1  10/2005  Kamal et al.

OTHER PUBLICATIONS

Kamal, A. et al., Synthesis and Antitumor Activity of Pyrene-linked Pyrrolo [2,1-c][1,4]benzodiazepine Hybrids, Bioorganic & Medicinal Chemical Letters, vol. 14, pp. 471-474 (2004).

*Primary Examiner* — Bruck Kifle
(74) *Attorney, Agent, or Firm* — Fitzpatrick, Cella, Harper & Scinto

(57) ABSTRACT

The present invention provides a compounds of general formula (6), useful as potential antitumour agents against human cancer cell lines. The present invention further provides a process for the preparation of pyrrolo[2,1-c][1,4]benzodiazepine hybrids of general formula (6).

6 Claims, 1 Drawing Sheet

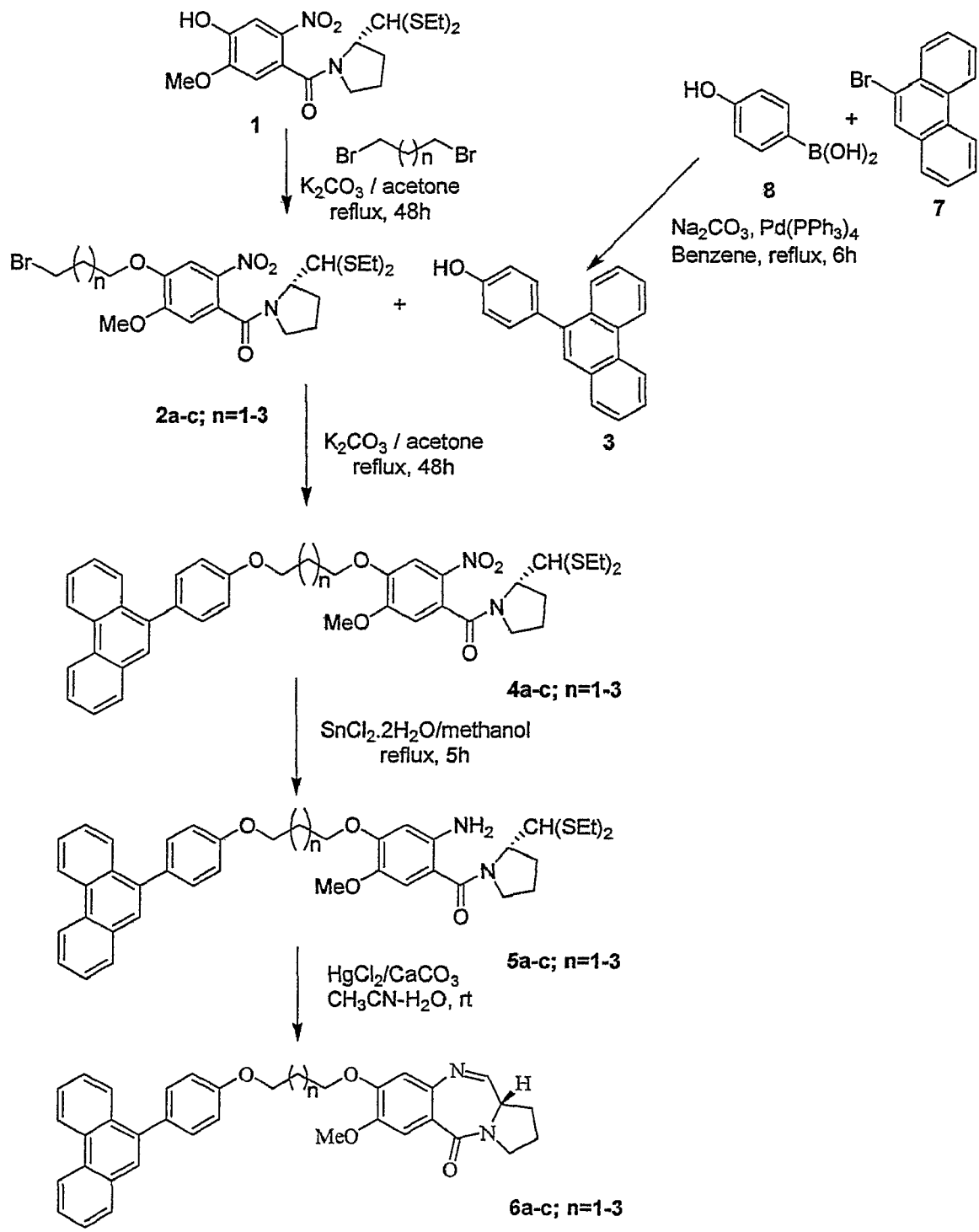

PHENANTHRYLPHENOL LINKED PYRROLO [2, L-C] [L, 4] BENZODIAZEPINE HYBRIDS AS POTENTIAL ANTITUMOUR AGENTS AND PROCESS FOR THE PREPARATION THEREOF

FIELD OF THE INVENTION

The present invention relates to a process for the preparation of new pyrrolo[2,1-c][1,4]benzodiazepine hybrids useful as potential antitumour agents. This invention relates to a process for the preparation of new pyrrolo[2,1-c][1,4]benzodiazepine hybrids as potential antitumour agents. More particularly, it provides a process for the preparation of (11aS)-7-methoxy-8-N-[4-(9-phenanthryl)phenoxy]alkoxy-2,3,5,11a-tetrahydro-1H-benzo[e]pyrrolo[1,2-a][1,4]-diazepin-5-one, with aliphatic chain length variation of these compounds and it also describes the DNA binding, anticancer (antitumour) activity. The structural formula of this new pyrrolo[2,1-c][1,4]benzodiazepine is given below:

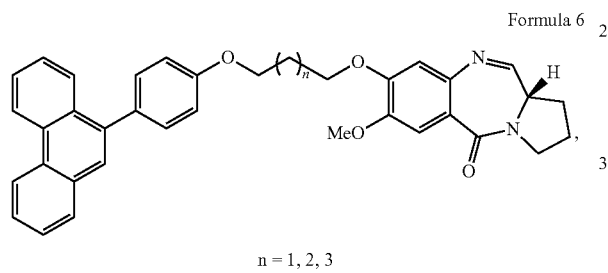

Formula 6 n = 1, 2, 3

BACKGROUND OF THE INVENTION

Pyrrolo[2,1-c][1,4]benzodiazepine antitumour antibiotics are commonly known as anthramycin class of compounds. In the last few years, a growing interest has been shown in the development of new pyrrolo[2,1-c][1,4]benzodiazepine (PBDs). These antibiotics react covalently with DNA to form an N2-guanine adduct that lies within the minor groove of duplex DNA via an acid-labile aminal bond to the electrophilic imine at the N10-C11 position (Kunimoto, S.; Masuda, T.; Kanbayashi, N.; Hamada, M.; Naganawa, H.; Miyamoto, M.; Takeuchi, T.; and Unezawa, H. *J. Antibiot.*, 1980, 33, 665.; Kohn, K. W. and Speous, C. L. *J. Mol. Biol.*, 1970, 51 551.; Hurley, L. H.; Gairpla, C. and Zmijewski, M. Biochem. *Biophys. Acta.*, 1977, 475, 521.; Kaplan, D. J. and Hurley, L. H. *Biochemistry*, 1981, 20, 7572). The molecules have a right-handed twist, which allows them to follow the curvature of the minor groove of B-form double-stranded DNA spanning three base pairs. Recently, PBD dimers have been developed that comprises two C2-exo methylene substituted DC-81 subunits tethered through their C-8 position via an inert propanedioxy linker (Gregson, S. J.; Howard, P. W.; Hartley, J. A.; Brooks, N. A.; Adams, L. J.; Jenkins, T. C.; Kelland, L. R. and Thurston, D. E. *J. Med. Chem.* 2001, 44, 737). A recent development has been the linking of two PBD units through their C-8 positions to give bisfunctional alkylating agents capable of cross-linking DNA (Thurston, D. E.; Bose, D. S.; Thomson, A. S.; Howard, P. W.; Leoni, A.; Croker, S. J.; Jenkins, T. C.; Neidle, S. and Hurley, L. H. *J. Org. Chem.* 1996, 61, 8141).

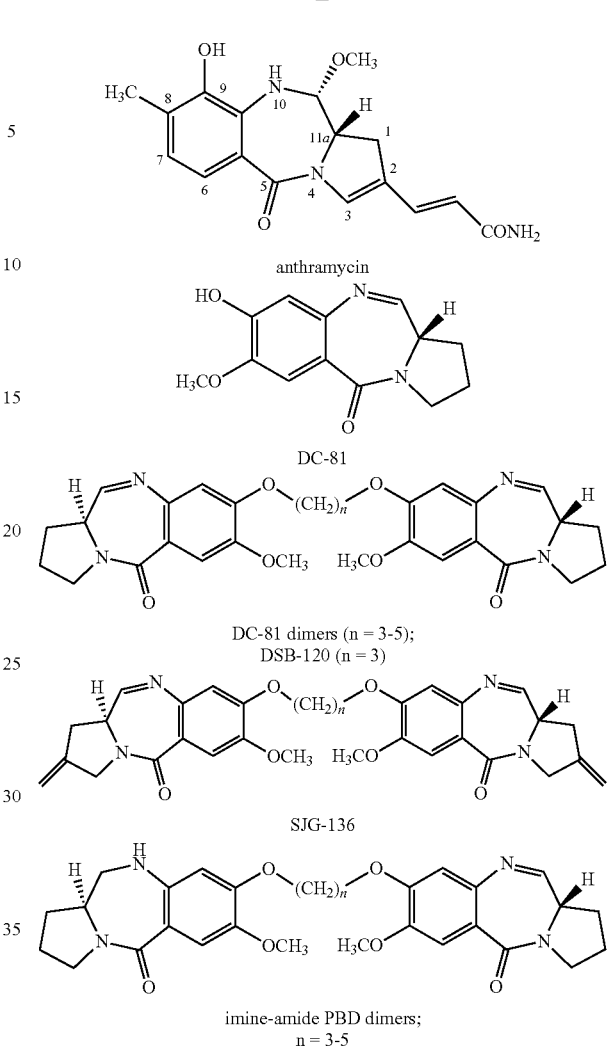

anthramycin

DC-81

DC-81 dimers (n = 3-5);
DSB-120 (n = 3)

SJG-136 imine-amide PBD dimers;
n = 3-5

A non-cross-linking mixed imine-amide PBD dimers have been synthesized that have significant DNA binding ability and potent antitumour activity (Kamal, A.; Ramesh, G. Laxman, N.; Ramulu, P.; Srinivas, O.; Neelima, K.; Kondapi, A. K.; Srinu, V. B.; Nagarajaram, H. M. *J. Med. Chem.* 2002, 45, 4679). Recently, some new pyrrolobenzodiazepine (PBD) hybrids have been synthesized that have significant DNA binding ability and potent antitumour activity (Kamal, A.; Srinivas, O.; Ramulu, P.; Ramesh, G.; Kumar, P. P. *Bioorg. Med. Chem. Lett.* 2003, 13, 3577).

Naturally occurring pyrrolo[2,1-c][1,4]benzodiazepines belong to a group of antitumour antibiotics derived from *Streptomyces* species. Recently, there is much impetus for the PBD systems as they can recognize and bind to specific sequence of DNA. Examples of naturally occurring PBDs include anthramycin, DC-81, tomaymycin, sibiromycin and neothramycin.

Phenanthrylphenol is small synthetic molecule that contains a phenanthrene ring coupled to a 4-hydroxy phenyl boronic acid (Suzuki cross-coupling reaction). A number of polyaromatic hydrocarbons (PAH) and their derivatives in view of their planar ring system are known to intercalate with DNA resulting in the anticancer activity (Venitt, S.; Crofton-Sleigh, C.; Agbandje, M.; Jenkins, T. C.; Neidle, S. *J. Med. Chem.* 1998, 41, 3748. Kamal, A.; Ramsh, G.; Srinivas, O.; Ramulu, P.; *Bioorg. Med. Chem. Lett.* 2004, 14, 471).

The structurally related phenanthrenes have also been reported to possess anticancer activity (Jones, B. G.; Mathews, J. E.; Banner, K. W. *Heterocycles*, 38, 6, 1994, Wei, L.; Brossi, A.; Kendall, R.; Bastow, K. F.; Natschke, S. L. M.; Shi. Q.; Lee. K. H.; *Bioorg. Med. Chem.* 2006, 14, 6560. Shagufa.; Srivastava, A. K.; Sharma, R.; Mishra, R.; Balapure, A. K.; Murthy, P. S. R.; Panda, G.; *Bioorg. Med. Chem.* 2006, 14, 1497). Based on the potent anticancer activity of pyrrolo[2,1-c][1,4]benzodiazepines, phenanthrenes, new PBD hybrids have been designed and synthesized by linking phenanthrylphenol moiety at C8-position of pyrrolo[2,1-c][1,4]benzodiazepine with varying alkane spacers.

OBJECTIVES OF THE INVENTION

The main objective of the present invention is to provide new phenanthrylphenol linked pyrrolo[2,1-c][1,4]benzodiazepine hybrids, useful as antitumour agents.

Yet another object of this invention is to provide a process for the preparation of new phenanthrylphenol linked pyrrolo[2,1-c][1,4]benzodiazepine hybrids.

SUMMARY OF THE INVENTION

Accordingly the present invention provides a new phenanthrylphenol linked pyrrolo[2,1-c][1,4]benzodiazepine hybrid of general formula 6.

Formula 6

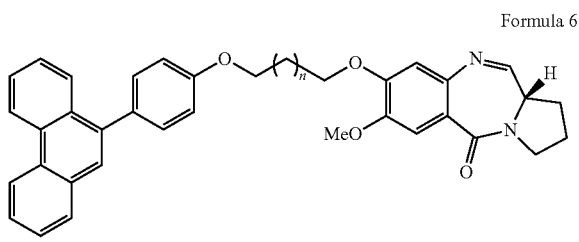

Where in, n = 1, 2, 3

The present invention provides a process for preparation of phenanthrylphenol linked pyrrolo[2,1-c][1,4]benzodiazepine hybrids of formula 6a-c which comprises of reacting (2S)-2-[di(ethylsulfanyl)methyl]tetrahydro-1H-1-pyrrolyl [4-hydroxy-5-(methyloxy)-2-nitrophenyl]methanone of formula 1 with dibromo Ames in presence of acetone/$K_2CO_3$ at reflux temperature for a period of 48 h, obtaining [4-(n-bromoalkoxy)-5-methoxy-2-nitrophenyl](2S)-2-[di(ethylsulfanyl)methyl]tetra-hydro-1H-1-pyrrolylmethanone of formula 2a-c (n=1-3), reacting these compounds with 4-(9-phenanthryl)phenol of formula 3, obtaining (2S)-2-[di (ethylsulfanyl)methyl]tetrahydro-1H-1-pyrrolyl(5-methoxy-2-nitro-4-n-[4-(9-phenanthryl)phenoxy]alkoxyphenyl) methanone of formula 4a-c (n=1-3), reducing the above nitro compounds of formula 4a-c with $SnCl_2.2H_2O$ in presence of organic solvent like methanol or ethanol up to a reflux temperature, obtaining the (2-amino-5-methoxy-4-n-[4-(9-phenanthryl)phenoxy]alkoxyphenyl)(2S)-2-[di(ethylsulfanyl)methyl]tetrahydro-1H-1-pyrrolylmethanone of formula 5a-c (n=1-3), reacting the above amino compounds of formula 5a-c (n=1-3) with known deprotecting agents in a conventional manner to give new pyrrolo[2,1-c][1,4]benzodiazepine hybrids of formula 6a-c (n=1-3).

DETAILED DESCRIPTION OF THE INVENTION

The precursors 4-(9-phenanthryl)phenol of formula 3 has been prepared by general procedure (Suzuki cross-coupling reaction) and (2S)-2-[di(ethylsulfanyl)methyl]tetrahydro-1H-1-pyrrolyl(4-hydroxy-5-methoxy-2-nitrophenyl)methanone of formula 1 (Thurston, D. E.; Murthy, V. S.; Langley, D. R.; Jones, G. B. *Synthesis*. 1990, 81) has been prepared by literature method. Some representative compounds of formula 6 for the present inventions are given below a) (11aS)-7-methoxy-8-3-[4-(9-phenanthryl)phenoxy] propoxy-2,3,5,11a-tetrahydro-1H-benzo[e]pyrrolo[1,2-a][1,4]diazepin-5-one (6a; n=1)

b) (11aS)-7-methoxy-8-4-[4-(9-phenanthryl)phenoxy]butoxy-2,3,5,11a-tetrahydro-1H-benzo[e]pyrrolo[1,2-a][1,4]diazepin-5-one (6b; n=2)

c) (11aS)-7-methoxy-8-(5-[4-(9-phenanthryl)phenoxy] pentyloxy)-2,3,5,11a-tetrahydro-1H-benzo[e]pyrrolo[1,2-a][1,4]diazepin-5-one (6c; n=3)

These new analogues of pyrrolo[2,1-c][1,4]benzodiazepine hybrids linked at C-8 position have shown promising DNA binding activity and efficient anticancer activity in various cell lines. The molecules synthesized are of immense biological significance with potential sequence selective DNA-binding property. This present invention is illustrated in FIG. 1 which comprises:

1) Synthesis of phenanthrylphenol from 9-bromophenanthrene and 4-hydroxy phenylborinic acid.
2) The ether linkage at C-8 position of DC-81 intermediates with phenanthrylphenol Moiety.
3) Refluxing the reaction mixtures for 48 h.
4) Synthesis of C-8 linked PBD antitumour antibiotic hybrid imines.
5) Purification by column chromatography using different solvents like ethyl acetate, hexane, chloroform and methanol.

The following examples are given by way of illustration of the working of the invention in actual practice and therefore should not be construed to limit the scope of present invention in any way.

EXAMPLE 1

To a solution of [4-(3-bromopropoxy)-5-methoxy-2-nitrophenyl](2S)-2-[di(ethyl-sulfanyl)methyl]tetrahydro-1H-1-pyrrolylmethanone 2a (535 mg, 1 mmol) in acetone (10 mL) was added anhydrous $K_2CO_3$ (552 mg, 4 mmol) and 4-(9-phenanthryl)phenol 3 (270 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using ethylacetate-hexane (1:1) as eluant to afford pure compound of 4a (568 mg, 80%).

$^1$H NMR (CDCl$_3$): δ 8.66-8.80 (m, 2H), 8.0 (s, 1H), 7.82-7.96 (m, 2H), 7.76 (s, 1H), 7.58-7.66 (m, 3H), 7.49-7.57 (d, 1H), 7.46 (d, 2H, J=8.648 Hz), 7.05 (d, 2H, J=8.648 Hz), 6.82 (s, 1H), 4.87 (d, 1H, J=3.60 Hz), 4.64-4.76 (m, 1H), 4.36 (t, 2H, J=6.486), 4.28 (t, 2H, J=5.765), 3.96 (s, 3H), 3.18-3.31 (m, 2H), 2.69-2.84 (m, 4H), 2.42 (p, 2H), 1.86-2.08 (m, 2H), 1.51-1.80 (m, 2H), 1.20-1.42 (m, 6H)

ESIMS: m/z 711 (M$^+$).

To compound 4a (711 mg, 1 mmol) in methanol (20 mL) was added SnCl$_2$.2H$_2$O (1.125 g, 5 mmol) and refluxed for 5 h or until the TLC indicated that reaction was completed. The methanol was evaporated under vacuum, the aqueous layer was then carefully adjusted to pH 8 with 10% NaHCO$_3$ solution and then extracted with ethylacetate and chloroform (2×30 mL and 2×30 mL). The combined organic phase was dried over Na$_2$SO$_4$ and evaporated under vacuum to afford the crude amino diethylthioacetal 5a (558 mg, 82%), which was used directly in the next step.

A solution of 5a (681 mg, 1 mmol), HgCl$_2$ (613 mg, 2.26 mmol) and CaCO$_3$ (246 mg, 2.46 mmol) in acetonitrile-water (4:1) was stirred slowly at room temperature for overnight. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (1%) to give compound 6a (333 mg, 60%). This material was repeatedly evaporated from CHCl$_3$ in vacuum to generate the imine form.

$^1$H NMR (CDCl$_3$): δ 8.71-8.83 (m, 2H), 7.88-7.99 (m, 2H), 7.67-7.72 (m, 3H), 7.58-7.67 (m, 3H), 7.56 (s, 1H), 7.47 (d, 2H, J=9.065 Hz), 7.08 (d, 2H, J=9.065 Hz), 6.92 (s, 1H), 4.28-4.38 (m, 4H), 3.98 (s, 3H), 3.79-3.92 (m, 1H), 3.70-3.76 (m, 1H), 2.39-2.49 (p, 2H), 2.28-2.37 (m, 2H), 2.02-2.12 (m, 2H).

LCMS: m/z 557.2 (M$^+$+1).

EXAMPLE 2

To a solution of [4-(4-bromobutoxy)-5-methoxy-2-nitrophenyl](2S)-2-[di(ethyl-sulfanyl)methyl]tetrahydro-1H-1-pyrrolylmethanone 2b (549 mg, 1 mmol) in acetone (10 mL) was added anhydrous K$_2$CO$_3$ (552 mg, 4 mmol) and 4-(9-phenanthryl)phenol 3 (270 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using ethylacetate-hexane (1:1) as eluant to afford pure compound of 4b (580 mg, 80%).

$^1$H NMR (CDCl$_3$): δ 8.66-8.80 (m, 2H), 8.0 (s, 1H), 7.82-7.96 (m, 2H), 7.76 (s, 1H), 7.58-7.66 (m, 3H), 7.49-7.57 (d, 1H), 7.46 (d, 2H, J=8.648 Hz), 7.05 (d, 2H, J=8.648 Hz), 6.82 (s, 1H), 4.87 (d, 1H, J=3.60 Hz), 4.64-4.76 (m, 1H), 4.11-4.26 (m, 4H), 3.96 (s, 3H), 3.20-3.33 (m, 2H), 2.69-2.87 (m, 4H), 2.00-2.19 (m, 4H), 1.88-1.99 (m, 1H), 1.74-1.83 (m, 1H), 1.54-1.73 (m, 2H), 1.1-1.41 (m, 6H)

ESIMS: m/z 725 (M$^+$).

To compound 4b (725 mg, 1 mmol) in methanol (20 mL) was added SnCl$_2$.2H$_2$O (1.125 g, 5 mmol) and refluxed for 5 h or until the TLC indicated that reaction was completed. The methanol was evaporated under vacuum, the aqueous layer was then carefully adjusted to pH 8 with 10% NaHCO$_3$ solution and then extracted with ethyl acetate and chloroform (2×30 mL and 2×30 mL). The combined organic phase was dried over Na$_2$SO$_4$ and evaporated under vacuum to afford the crude amino diethylthioacetal 5b (569 mg, 82%), which was used directly in the next step.

A solution of 5b (695 mg, 1 mmol), HgCl$_2$ (613 mg, 2.26 mmol) and CaCO$_3$ (246 mg, 2.46 mmol) in acetonitrile-water (4:1) was stirred slowly at room temperature for overnight. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (1%) to give compound 6b (342 mg, 60%). This material was repeatedly evaporated from CHCl$_3$ in vacuum to generate the imine form.

$^1$H NMR (CDCl$_3$): δ 8.70-8.80 (m, 2H), 7.86-7.98 (m, 2H), 7.67-7.70 (m, 3H), 7.55-7.62 (m, 3H), 7.53 (s, 1H), 7.46 (d, 2H, J=8.309 Hz), 7.05 (d, 2H, J=9.065 Hz), 6.85 (s, 1H), 4.10-4.26 (m, 4H); 3.96 (s, 3H), 3.78-3.86 (m, 1H), 3.69-3.77 (m, 1H), 2.27-2.34 (m, 2H), 2.00-2.18 (m, 4H), 1.23-1.29 (m, 2H).

LCMS: m/z 571.2 (M$^+$+1).

EXAMPLE 3

To a solution of 4-[(5-bromopentyl)oxy]-5-methoxy-2-nitrophenyl(2S)-2-[di(ethyl-sulfanyl)methyl]tetrahydro-1H-1-pyrrolylmethanone 2c (563 mg, 1 mmol) in acetone (10 mL) was added anhydrous K$_2$CO$_3$ (552 mg, 4 mmol) and 4-(9-phenanthryl)phenol 3 (270 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using ethylacetate-hexane (1:1) as eluant to afford pure compound of 4c (591 mg, 80%).

$^1$H NMR (CDCl$_3$): δ 8.67-8.77 (m, 2H); 8.00 (s, 1H), 7.83-7.95 (m, 2H), 7.67 (s, 1H), 7.57-7.64 (m, 3H), 7.48-7.56 (m, 1H), 7.44 (d, 2H, J=8.309 Hz), 7.01 (d, 2H, J=9.065 Hz), 6.81 (s, 1H), 4.84 (d, 1H, J=3.77 Hz), 4.65-4.73 (m, 1H), 4.07-4.19 (m, 4H), 3.96 (s, 3H), 3.18-3.33 (m, 2H), 2.64-2.87 (m, 4H), 2.18-2.34 (m, 4H), 1.90-2.14 (m, 3H), 1.71-1.85 (m, 1H), 1.48-1.59 (m, 2H), 1.21-1.42 (m, 6H)

ESIMS: m/z 739 (M$^+$).

To compound 4c (739 mg, 1 mmol) in methanol (20 mL) was added SnCl$_2$.2H$_2$O (1.125 g, 5 mmol) and refluxed for 5 h or until the TLC indicated that reaction was completed. The methanol was evaporated under vacuum, the aqueous layer was then carefully adjusted to pH 8 with 10% NaHCO$_3$ solution and then extracted with ethyl acetate and chloroform (2×30 mL and 2×30 mT,). The combined organic phase was dried over Na$_2$SO$_4$ and evaporated under vacuum to afford the crude amino diethylthioacetal 5c (581 mg, 82%), which was used directly in the next step.

A solution of 5c (709 mg, 1 mmol), HgCl$_2$ (613 mg, 2.26 mmol) and CaCO$_3$ (246 mg, 2.46 mmol) in acetonitrile-water (4:1) was stirred slowly at room temperature for overnight. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified, by column chromatography using MeOH—CHCl$_3$ (1%) to give compound 6c (350 mg, 60%). This material was repeatedly evaporated from CHCl$_3$ in vacuum to generate the imine form.

$^1$H NMR (CDCl$_3$): δ 8.68-8.83 (m, 2H), 7.85-8.01 (m, 2H), 7.56-7.63 (m, 3H), 7.64-7.75 (m, 3H), 7.54 (s, 1H), 7.47 (d, 2H, J=8.594 Hz), 7.05 (d, 2H, J=7.813 Hz), 6.85 (s, 1H), 3.99-4.27 (m, 4H), 3.96 (s, 3H), 3.70-3.92 (m, 1H), 3.54-3.66 (m, 1H), 2.21-2.44 (m, 2H), 1.85-2.16 (m, 4H), 1.54-1.83 (m, 2H), 1.19-1.35 (m, 2H)

LCMS: m/z 585.2 (M$^+$+1).

Biological Activity:
DNA Binding Affinity of new Phenanthrylphenol Linked PBD Hybrids (6a-c):

Compounds have been subjected to thermal denaturation studies with duplex-form calf thymus DNA (CT-DNA) using a modification of a reported procedure (Newman, M. S. *Carcinog-compr. Surv.* 1976, 1, 203; (b) Hecht, S. S.; Loy, M.; Hoffman, *Carcinog-compr. Surv.* 1976, 1, 325). Working solutions in aqueous buffer (10 mM NaH$_2$PO$_4$/Na$_2$HPO$_4$, 1 mM $Na_2EDTA$, pH 7.00+0.01) containing CT-DNA (100 µm in phosphate) and the PBD (20 µm) have been prepared by addition of concentrated PBD solutions in DMSO to obtain a fixed [PBD]/[DNA] molar ratio of 1:5. The DNA-PBD solutions have been incubated at 37° C. for 0 and 18 h prior to analysis. Samples have been monitored at 260 nm using a Beckman DU-800 spectrophotometer fitted with high performance temperature controller, and heated at 1° C. $min^{-1}$ in the 40-110° C. range. DNA helix→coil transition temperatures ($T_m$) have been obtained from the maxima in the $d(A_{260})/dT$ derivative plots. Drug-induced alterations in DNA melting behavior are given by: $\Delta T_m = T_m(DNA+PBD) - T_m(DNA$ alone), where the $T_m$ value for the PBD-free CT-DNA is 69.1±0.01. The fixed [PBD]/[DNA] ratio used has not resulted in binding saturation of the host DNA duplex for any compound examined.

The DNA binding activity for these new C8-linked phenanthrylphenol-PBD hybrids has been examined by thermal denaturation studies using calf thymus (CT) DNA. Melting studies show that these compounds stabilize the thermal helix→coil or melting stabilization ($\Delta T_m$) for the CT-DNA duplex at pH 7.0, incubated at 37° C., where PBD/DNA molar ratio is 1:5. The data for the compounds 6a-c is included in Table 1 for comparison.

TABLE 1

Thermal denaturation data for phenanthryl phenol linked PBD hybrids with calf thymus (CT) DNA

| PBD hybrids | [PBD]:[DNA] molar ratio[b] | ($\Delta T_m$ ° C.)[a] after incubation at 37° C. for | |
|---|---|---|---|
| | | 0 h | 18 h |
| 6a | 1:5 | 1.0 | 1.8 |
| 6b | 1:5 | 0.3 | 0.5 |
| 6c | 1:5 | 0.1 | 0.2 |
| DC-81 | 1:5 | 0.3 | 0.7 |

[a]For CT-DNA alone at pH 7.00 ± 0.01, $T_m$ = 69.1° C. ± 0.01 (mean value from 10 separate determinations), all $\Delta T_m$ values are ± 0.1-0.2° C.
[b]For a 1:5 molar ratio of [PBD]/[DNA], where CT-DNA concentration = 100 µM and ligand concentration = 20 µM in aqueous sodium phosphate buffer [10 mM sodium phosphate + 1 mM EDTA, pH 7.00 ± 0.01].

Anticancer Activity:

The compounds 6a-c (n=1-3) were examined for preliminary in vitro cytotoxicity on six cell lines, among these compound's 6a has shown promising activity as shown in Table 2 and was further taken up detailed in vitro anticancer activity at the National Cancer Institute, Maryland, USA.

TABLE 2

Preliminary in vitro cytotoxicity data for the compounds 6a-c at concentration (mg/ml) 1 × $10^{-5}$M.

| compound | Lung A-549 | Colon HCT-15 | Neuroblastoma IMR-32 | Ovary OVCAR-5 | Liver HEP-2 | Colon 502713 |
|---|---|---|---|---|---|---|
| 6a | 88 | 99 | 85 | 98 | 58 | 69 |
| 6b | 50 | 77 | 67 | 93 | 49 | 72 |
| 6c | 36 | 79 | 73 | 98 | 65 | 74 |

The compound 6a was evaluated for in vitro anticancer activity against sixty human tumour cells derived from nine cancer panels (leukemia, non-small-cell lung, colon, CNS, melanoma, ovarian, prostate, renal and breast cancer) as shown in Table 4. For compound 6a, dose response curves for each cell line were measured at a minimum of five concentrations at 10 fold dilutions. A protocol of 48 h continuous drug exposure was used and a sulforhodamine B (SRB) protein assay was used to estimate cell viability or growth. The concentration causing 50% cell growth inhibition (GI50), total cell growth inhibition (TGI 0% growth) and 50% cell death (LC50, 50% growth) compared with the control was calculated. The mean graph midpoint values of $\log_{10}$ TGI and $\log_{10}$ LC50 as well as $\log_{10}$ GI50 for 6a listed in Table 3. As demonstrated by mean graph pattern, compound 6a exhibits an interesting profile of activity and selectivity for various cell lines. The mean graph mid point of $\log_{10}$ TGI and $\log_{10}$ LC50 showed similar pattern to the $\log_{10}$ GI50 mean graph mid points.

TABLE 3

$\log_{10}$ GI50 $\log_{10}$ TGI and $\log_{10}$ LC50 mean graphs midpoints (MG_MID) of in vitro cytotoxicity data for the representative compounds against human tumour cell lines

| Compound | $\log_{10}$ GI50 | $\log_{10}$ TGI | $\log_{10}$ LC50 |
|---|---|---|---|
| 6a | −6.28 | −5.76 | −5.26 |

TABLE 4

$\log_{10}$ GI50 (concentration in mol/L) and $\log_{10}$ LC50 (concentration in mol/L causing 50% lethality) values for the representative compound 6a

| Cancer panel | $\log_{10}$ GI50 | $\log_{10}$ LC50 |
|---|---|---|
| Leukemia | −6.71 | −4.82 |
| Non-small-cell-lung | −6.11 | −5.27 |
| Colon | −6.11 | −5.31 |
| CNS | −6.09 | −5.33 |
| Melanoma | −6.16 | −5.33 |
| Ovarian | −6.30 | −5.43 |
| Renal | −6.31 | −5.44 |
| Prostate | −6.40 | −5.41 |
| Breast | −6.47 | −5.06 |

Each cancer type represents the average of six to nine different cancer cell lines.

We claim:
1. A compound of formula 6:

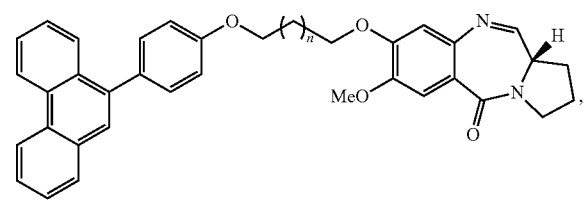

wherein n is 1, 2, or 3.

2. The compound of claim 1, having a structural formula 6a:

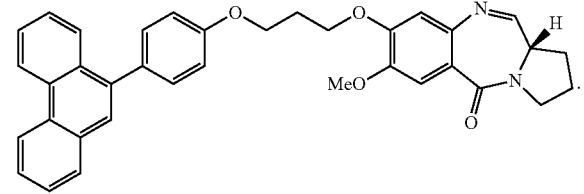

3. The compound of claim 1, having a structural formula 6b:

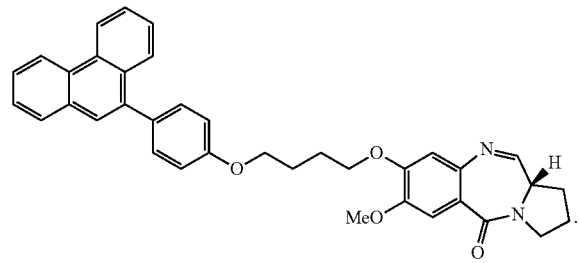

4. The compound of claim 1, having a structural formula 6c:

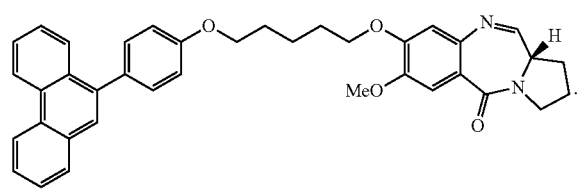

5. A process for preparing compound of formula 6:

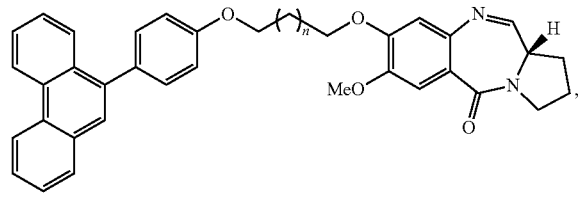

wherein n is 1, 2, or 3, said process comprising the steps of:
a) reacting [4-(n-bromoalkoxy)-5-methoxy-2-nitrophenyl](2S)-2-[di(ethylsulfanyl)methyl]tetrahydro-1H-1-pyrrolylmethanone of formula 2a-c:

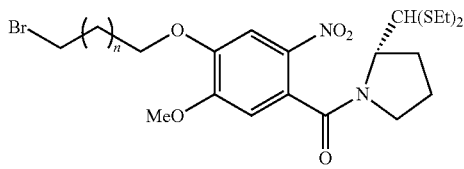

with phenanthryl phenol of formula 3:

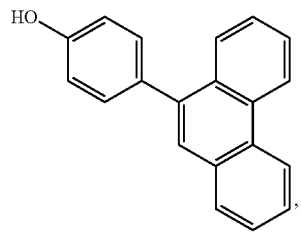

to obtain (2S)-2-[di(ethyl sulfanyl)methyl]-tetrahydro-1H-1-pyrrolyl (5-methoxy-2-nitro-4-n-[4-(9-phenanthryl)phenoxy]alkoxyphenyl)methanone of formula 4a-c:

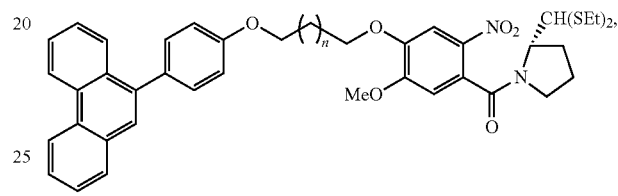

wherein n is 1, 2, or 3;
b) reducing the compound of formula 4a-c with $SnCl_2 \cdot 2H_2O$ in the presence of an organic solvent up to a reflux temperature, to obtain (2-amino-5-methoxy-4-n-[4-(9-phenanthryl)phenoxy]alkoxyphenyl)(2R)-2-[di(ethylsulfanyl)methyl]tetrahydro-1H-1-pyrrolyl methanone of formula 5a-c:

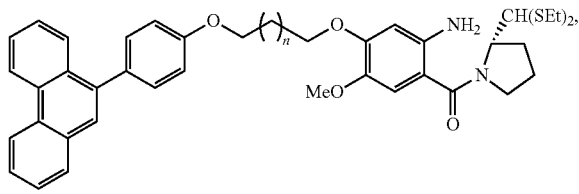

wherein n is 1, 2, or 3; and
c) reacting the compound of formula 5a-c with a deprotecting agent to obtain the compound of formula 6.

6. The process of claim 5, wherein the organic solvent is methanol or ethanol.

* * * * *

UNITED STATES PATENT AND TRADEMARK OFFICE
CERTIFICATE OF CORRECTION

PATENT NO. : 8,217,167 B2  Page 1 of 1
APPLICATION NO. : 12/922123
DATED : July 10, 2012
INVENTOR(S) : Kamal Ahmed et al.

It is certified that error appears in the above-identified patent and that said Letters Patent is hereby corrected as shown below:

Title Page, Item [54] and Column 1, Lines 1-5, Title,

"PHENANTHRYLPHENOL LINKED PYRROLO [2, L-*C*] [L, 4] BENZODIAZEPINE HYBRIDS AS POTENTIAL ANTITUMOUR AGENTS AND PROCESS FOR THE PREPARATION THEREOF" should read --NEW PHENANTHRYLPHENOL LINKED PYRROLO [2, 1-C][1, 4] BENZODIAZEPINE HYBRIDS AS POTENTIAL ANTITUMOUR AGENTS AND PROCESS FOR THE PREPARATION THEREOF--.

Signed and Sealed this
Eighteenth Day of December, 2012

David J. Kappos
*Director of the United States Patent and Trademark Office*

UNITED STATES PATENT AND TRADEMARK OFFICE
CERTIFICATE OF CORRECTION

PATENT NO. : 8,217,167 B2
APPLICATION NO. : 12/922123
DATED : July 10, 2012
INVENTOR(S) : Kamal Ahmed et al.

Page 1 of 1

It is certified that error appears in the above-identified patent and that said Letters Patent is hereby corrected as shown below:

Title Page,
Item [54], Title, the word "NEW" (as inserted by the Certificate of Correction issued December 18, 2012) should be deleted and title is reinstated to read --PHENANTHRYLPHENOL LINKED PYRROLO [2, L-C] [L, 4] BENZODIAZEPINE HYBRIDS AS POTENTIAL ANTITUMOUR AGENTS AND PROCESS FOR THE PREPARATION THEREOF--.

Signed and Sealed this
Fifth Day of February, 2013

Teresa Stanek Rea
*Acting Director of the United States Patent and Trademark Office*